United States Patent
Okuda

(10) Patent No.: US 6,177,991 B1
(45) Date of Patent: *Jan. 23, 2001

(54) MEASURING DEVICE WITH AUTOMATIC SAMPLE CHANGER

(75) Inventor: Tetsuo Okuda, Osaka (JP)

(73) Assignee: Shimadzu Corporation, Kyoto (JP)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/188,751

(22) Filed: Nov. 9, 1998

(30) Foreign Application Priority Data

Dec. 26, 1997 (JP) .................................... 9-368799

(51) Int. Cl.$^7$ ........................................ G01J 3/28
(52) U.S. Cl. ............................. 356/326; 300/72
(58) Field of Search .................. 356/326, 300, 356/72

(56) References Cited

U.S. PATENT DOCUMENTS 4,024,395 * 5/1977 Mueller et al. ................. 200/328
4,582,990 * 4/1986 Stevens ........................... 200/328

* cited by examiner

Primary Examiner—Frank G. Font
Assistant Examiner—Reginald A. Ratliff
(74) Attorney, Agent, or Firm—Majestic, Parsons, Siebert & Hsue P.C.

(57) ABSTRACT

A measuring device such as a spectrometer uses an automatic sample changer for carrying a plurality of samples. The automatic sample changer may include a rotary circular disk rotatable around its central shaft by a stepping motor for changing positions of the samples which are positioned in a circle around the central shaft of the disk. A memory device preliminarily storing control data for each of different kinds of automatic sample changers is provided. The automatic sample changer, when connected to a control unit in the main body, serves to receive control signals for controlling motions of the motor and to transmit data stored in the memory device through a connector. The main body of the measuring device contains a control unit which serves to read out the control data from the memory device, to use the received control data to generate the control signal and to transmit the generated control signal to the automatic sample changer.

10 Claims, 3 Drawing Sheets

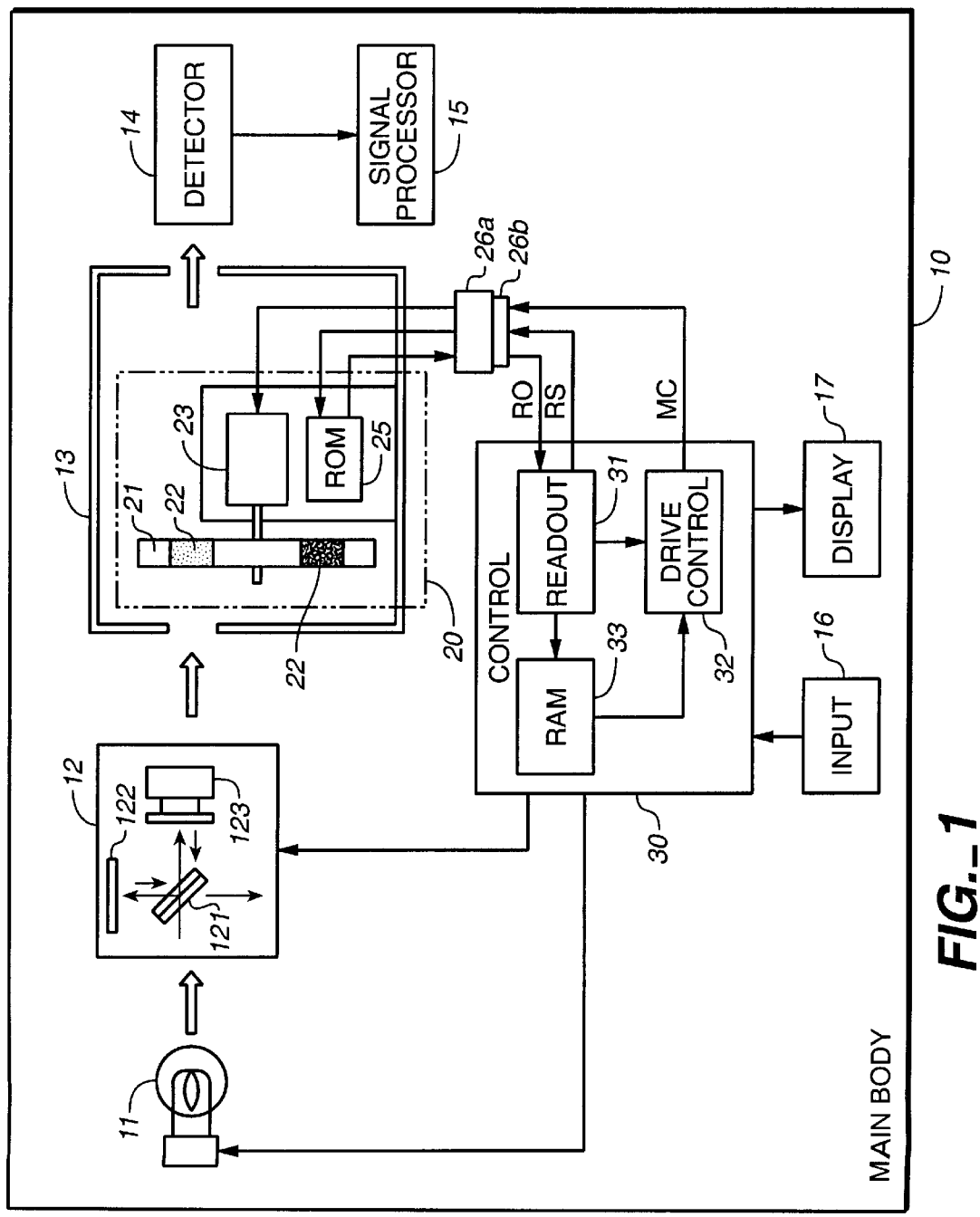
FIG._1

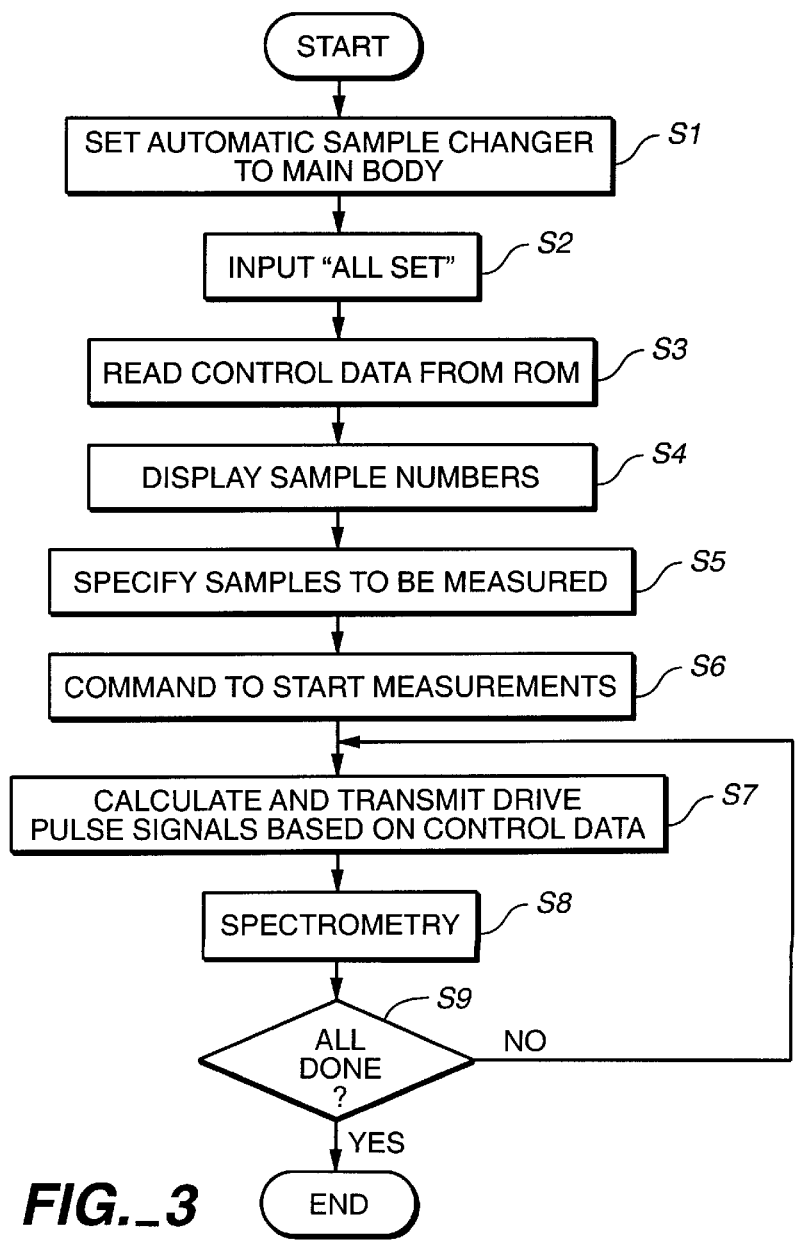

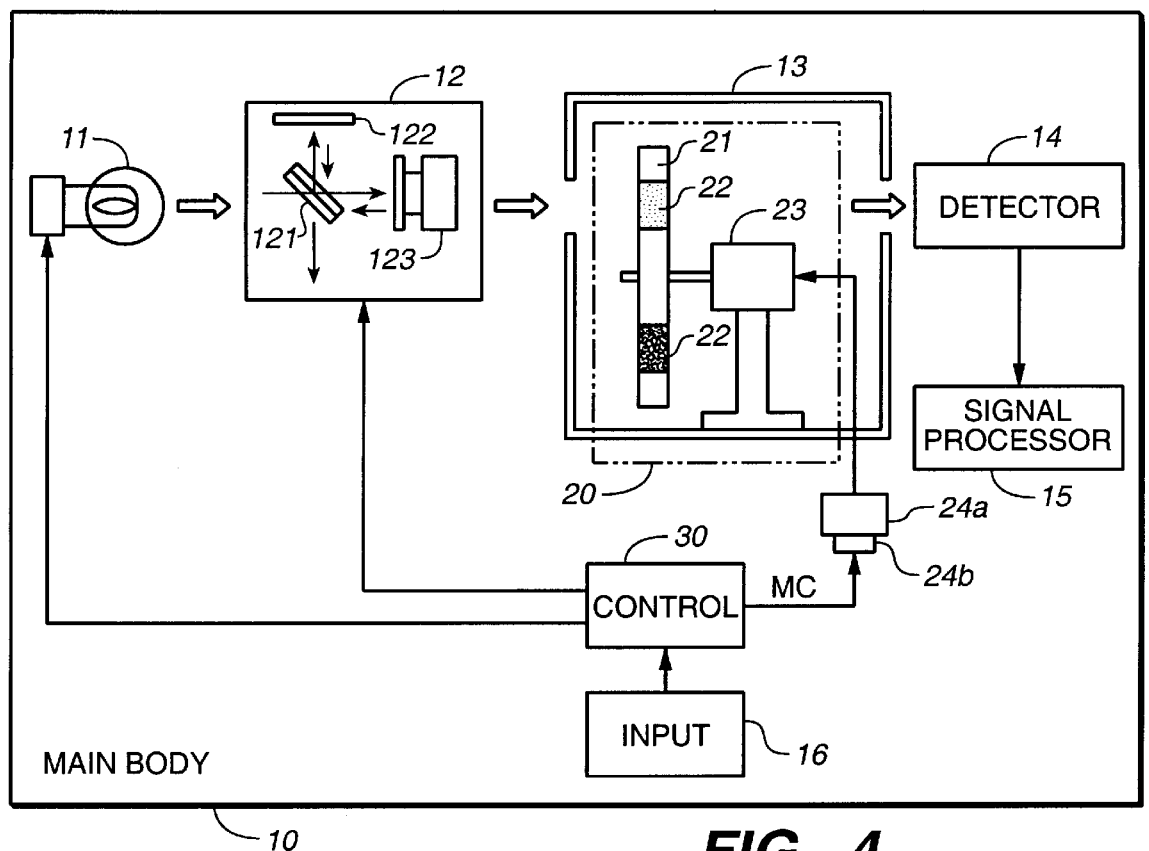
FIG._4
*(PRIOR ART)*
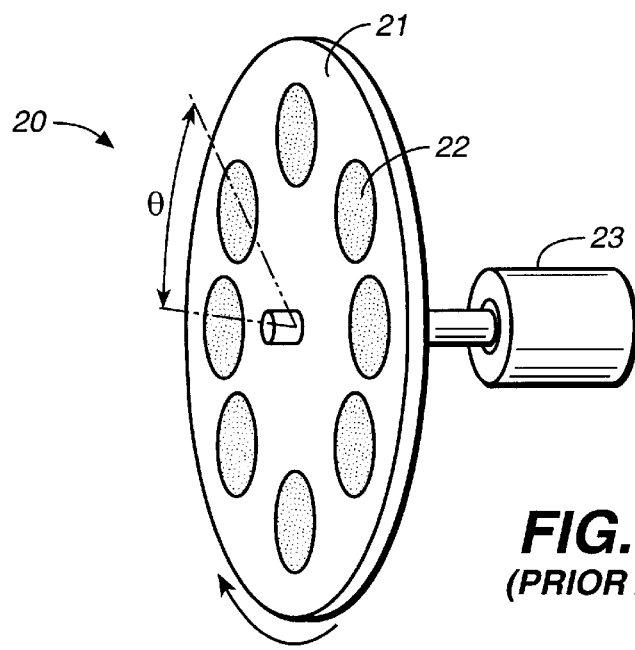
FIG._5
*(PRIOR ART)*

MEASURING DEVICE WITH AUTOMATIC SAMPLE CHANGER

BACKGROUND OF THE INVENTION

This invention relates to a measuring device with the capability of automatically exchanging samples, comprising an automatic sample changer on which a plurality of samples can be selectably set and a main body which contains a control unit for controlling the operation of this automatic sample changer for selecting a sample. Such a measuring device can be utilized in a spectrometer using an automatic sample changer having a plurality of samples set along the outer periphery of a rotatable circular disk.

When it is desired to measure a plurality of samples continuously, one frequently uses an accessory device such as an automatic sample changer or an automatic sampler adapted to automatically select or exchange a plurality of samples and transport them to a specified position for the measurement. With the help of such an accessory device, the user can set up all the desired samples prior to the beginning of the measurements and need not necessarily be present when the measurements are actually being carried out until automatic measurements of all the samples are completed. Such a procedure is particularly effective if the samples to be measured are relatively stable chemically and do not require any chemical pretreatment.

In general, most samples suitable for infrared spectrometry satisfy these conditions, and automatic measurements are frequently carried out by using an automatic sample changer. FIG. 4 shows schematically a prior art Fourier transform infrared spectrometer which may be roughly described as comprising a main body 10 including a sample chamber 13 and an automatic sample changer 20 which is detachably attached to this sample chamber 13. Infrared light emitted from a source 11 inside the main body 10 is introduced to an interferometer (the "optical means") 12. The interferometer 12 includes a beam splitter 121, a fixed mirror 122 and a longitudinally slidable mobile mirror 123. The reflected beams from the fixed mirror 122 and the mobile mirror 123 are lead by the beam splitter 121 to propagate in a same direction, resulting in a coherent infrared light beam with amplitude which varies time-wise. This coherent infrared light beam is lead into the sample chamber 13 and directed to one of the sample cells 22 on the automatic sample changer 20. The gas, liquid or solid sample inside the sample cell 22 absorbs the light with characteristic wavelengths, depending on its constituents. The light which passes through the sample cell 22 is lead out of the sample chamber 13 and detected by a detector 14. What is outputted from the detector 14 is an intensity signal as a function of time, and this is Fourier-transformed to obtain a relationship between the frequency (or wavelength of light) and the signal intensity. Thus, the signal outputted from the detector 14 is Fourier-transformed by a signal processor 15 which serves to generate an absorption spectrum. If necessary, this absorption spectrum may be used to calculate the spectral absorptivity and transmissivity.

FIG. 5 shows an example of automatic sample changer 20 having a plurality of sample cells 22 arranged in a circle along the outer periphery of a circular rotary disk 21. The central shaft of this disk 21 is driven directly or indirectly (such as through a suitable decelerating mechanism) by a motor 23 to be rotated. Control signals MC to the motor 23 for selecting a sample cell 22 is provided from a control unit 30 through connectors 24a and 24b.

In general, automatic sample changers of different kinds are provided such as those for carrying different numbers of sample cells, depending, for example, on the sizes of the samples and those having a selected reference sample already set in one part such that a most suitable automatic sample changer can be selected and set inside the sample chamber 13 according to the purpose of and the target for the measurement. If the number of sample cells is different, for example, the angular separation θ between mutually adjacent sample cells 22 will also be different and hence the control unit 30 is required to control the motion of the motor 23 differently to select a sample cell, depending on the kind of automatic sample changer which has been set.

With a prior art device of this type, therefore, the user had to input through an input device 16 (such as a keyboard) the distribution of the sample cells (such as their angular separations θ and their number) or the position of the reference sample, depending on the type of the installed automatic sample changer. Such an input work is a troublesome procedure and since the user seldom remembers the method of such operations, the user is compelled to make the input by consulting a document such as an instruction book. In summary, such a prior art device was not efficient.

In view of the above, it has been proposed to provide the control unit 30 with the function of identifying the kind of automatic sample changer which has been installed. This may be accomplished, for example, by providing each automatic sample changer 20 with a connector having a plurality of pins such that each automatic sample changer has a different connection scheme for the pins. As an automatic sample changer 20 is set inside the sample chamber 13 and a connecter from the control unit 30 is engaged with the connector on the automatic sample changer, the control unit 30 can identify the type of the automatic sample changer 20 from the condition of the connection of each pin.

With this method, however, the number of different kinds of automatic sample changer that can be identified is limited, depending on the number of the pins on the connector. Since the control unit 30 can identify only the kinds of automatic sample changer which have originally been encoded, it cannot identify any automatic sample changer of a novel structure which did not exist when the encoder was prepared. In other words, extendability of use is very poor with such a scheme.

SUMMARY OF THE INVENTION

It is therefore an object of this invention in view of the above to provide an improved measuring device capable of using many different kinds of automatic sample changers without the necessity of a cumbersome input procedure.

A measuring device embodying this invention, with which the above and other objects can be accomplished, may be characterized as comprising an automatic sample changer for carrying a plurality of samples thereon and a main body. The automatic sample changer may include a rotary circular disk rotatable around its central shaft by a stepping motor for changing positions of the samples thereon which, for example, may be positioned in a circle around the central shaft of the disk. A memory device preliminarily storing control data for each of different kinds of automatic sample changers is provided.

The automatic sample changer, when connected to a control unit in the main body, serves to receive control signals for controlling motions of the motor and to transmit data stored in the memory device through a connector. The main body contains a readout means for reading out the control data from the memory device, a drive control means for using the control data received by the readout means to generate the control signal and to transmit the generated control signal to the automatic sample changer.

BRIEF DESCRIPTION OF THE DRAWINGS

The accompanying drawings, which are incorporated in and form a part of this specification, illustrate an embodiment of the invention and, together with the description, serve to explain the principles of the invention. In the drawings:

FIG. 1 is a schematic block diagram of a spectrometer embodying this invention;

FIG. 2 is a schematic conceptual diagram of control data stored in a ROM contained in an automatic sample changer of this example;

FIG. 3 is a flow chart of a measurement operation by this example;

FIG. 4 is a schematic block diagram of a prior art spectrometer of a common type; and FIG. 5 is a diagonal external view of an automatic sample changer.

Throughout herein, like or equivalent components may be indicated by the same numerals even where they are components of different devices and may not necessarily be described repetitiously.

DETAILED DESCRIPTION OF THE INVENTION

In what follows, the invention will be described with reference to FIGS. 1–3 as applied to a Fourier transform infrared spectrometer.

As shown in FIG. 1, the automatic sample changer 20 according to this example contains a ROM 25 in which control data as shown in FIG. 2 are preliminarily (say, when it is shipped from a factory) stored. Readout control signals RS, output signals RO and drive control signals MC for the motor 23 are inputted to and outputted from the ROM 25 through a connector 26a. The motor 23 is a stepping motor having a mechanical stopped for defining its reference angular position, and its rotor is adapted to rotate from this reference angular position by an angle specified by the number of pulse drive signals inputted as the drive control signal MC. Although FIG. 1 shows the shaft of the rotary disk 21 directly connected to the drive shaft of the motor 23 to form a so-called direct drive mechanism, a suitable decelerating mechanism may be inserted therebetween. Although not shown, a power source for the motor 23 and the ROM 25 is adapted to supply power also through the connector 26a.

The aforementioned control signals contain data which are particular to the structure of the automatic sample changer 20, such as shown in FIG. 2, including sample numbers, the angular positions (measured from the reference angular position) of the sample cells identified by these sample numbers and the kind of the samples (whether the reference sample ("REFERENCE") preliminarily set or a sample "UNKNOWN" set by the user).

The control unit 30 in the main body 10 of the spectrometer includes a readout part 31, a drive control part 32 and a RAM 33. The readout part 31 serves to output readout control signals RS to the ROM 25 and, as the ROM 25 outputs output signals RO in response, to read in these output signals RO sequentially and store them temporarily in the RAM 33. The readout signals RS may be adapted to directly specify addresses in the ROM 25. Alternatively, the ROM 25 may include an address-generating circuit (say, comprising a counter) and the readout signals RS may serve to provide a reset signal or a clock signal for activating this address-generating circuit.

The drive control part 32 contains a ROM in which is preliminarily stored the relationship between the angle of rotation of the rotor of the motor 23 (that is, that of the rotary disk 21) and the number of pulse drive signals. As will be described below more in detail, the control data for the automatic sample changer 20 stored in the RAM 33 are made use of such that appropriate drive control signals MC are outputted so as to bring a desired one of the sample cells 22 to the incident position of the measuring light.

The aforementioned control unit 30 and signal processor 15 may be realized by an ordinary personal computer provided with a specified software program. In such a case, the input device 16 may be realized by an input means for such a personal computer such as a keyboard and/or a mouse, and the display (shown at 17 in FIG. 1) may represent a device such as a CRT or a liquid crystal display device.

Next, the flowchart of FIG. 3 is referenced to explain the operation for measurements with the spectrometer described above. First, the user sets desired samples to be measured in the sample cells 22 on the automatic sample changer 20. It now goes without saying that it is not necessary that all of the sample cells 22 should be used. Thereafter, this automatic sample changer 20 is installed inside the sample chamber 13 of the main body 10 and the connectors ("the first connector 26a" and "the second connector 26b") are connected together (Step S1). Next, the user carries out a specified input operation such as pressing an "ALL SET" button, thereby causing readout signals RS to be transmitted from the readout part 31 through the connectors 26a and 26b to the ROM 25 (Step S2). In response, the ROM 25 transmits corresponding control data as shown in FIG. 2 and these data are caused to be stored in specified regions of the RAM 33 (Step S3). On the basis of these data, the control unit 30 causes all the sample numbers of the sample cells on the automatic sample changer 20 to be displayed on the screen of the display device 17 (Step S4).

The user looks at this display and specifies the sample numbers of the samples to be measured in the order in which they are to be measured, as well as the method of measurement (such as the transmissivity and absorptivity modes) and, if desired, conditions of the measurements (Step S5). The control program may be so designed that the user can also input convenient additional data corresponding to the individual sample numbers, such as the names of the samples, through the input device 16.

Once all these input operations are completed, the user sends a command to start the measurements (Step S6). When this command is received, the drive control part 32 reads out from the RAM 33 the angles of rotation corresponding to the sample numbers selected by the user in the specified order, determines the corresponding numbers of pulse signals on the basis of the relationship between the angle of rotation and the number of drive pulses and outputs for each of the selected sample numbers the determined number of drive pulses (as the drive control signal MC) (Step S7). The motor 23 rotates by a small angle in response to each of these drive pulse signals, stopping when the specified sample cell 22 reaches the position of the incident light. A spectrometric process is carried out thereafter and the light which has passed through the sample cell reaches the detector 14. A corresponding detection signal is thus received by the signal processor 15, which creates an absorption spectrum of the sample (Step S8).

The control unit 30 then examines whether all the samples specified by the user have been thus measured (Step S9). If there are still samples to be measured, the program returns to Step S7, and the drive control part 32 serves to read out from the RAM 33 the angle of rotation corresponding to the sample number which is next in the order specified by the user. The process described above is repeated automatically for the next selected sample number until the measurements are completed on all of the specified sample numbers (Yes in Step S9).

The user may input a command, prior to the start of the measurements, to carry out the measurement on a reference sample (if it has been set) whether at the beginning, at the end or at any convenient point in time in between such that the control unit 30 controls the rotary motion of the motor 23 accordingly because the control unit 30 can identify from the data stored as shown in FIG. 2 that the reference sample corresponds to the sample number "1" in this example.

Advantages of this invention should be apparent. When a different automatic sample changer with a different number of sample cells is set, the final sample number at the bottom in the table of FIG. 2 is usually also different, as well as the angles of rotation corresponding to the individual sample cells. Since the readout part 31 serves to read out control data from the ROM 25 each time before starting a series of measurements and to rewrite the contents of the RAM 33, the user is not required to go through the trouble of inputting these data in order to carry out measurements correctly.

Although the invention has been described above with reference to only one example, this example is not intended to limit the scope of the invention. Many modifications and variations are possible within the scope of the invention. For example, although a standard white plate or the like is usually used as "the reference sample" for the calculation of a reference value of absorptivity or transmissivity, any selected sample having a specific characteristic may be used, for example, for comparison when the absorption spectrum or the like of an unknown sample is being evaluated. In an application to spectrometry, furthermore, a film, a glass piece, a filter and/or a prism having specified particular characteristics may be installed, instead of sample cells 22, on the rotary disk 21, although not separately illustrated. When samples on such an automatic sample changers are thus measured automatically, it is preferable that the types of these samples be included in the aforementioned control data and it is even more preferable to include the conditions of measurement corresponding to each sample such that each component of the measuring device can be automatically adjusted by the control unit 30.

Although a rotary system was disclosed in FIG. 1 for selecting sample cells, use may be made of a rack containing a plurality of sample vials in a plane and movable in its plane or also additionally in the perpendicular direction such that a vial or a sample in a vial at a specified position on the rack can be retrieved. If such a moving system is used, the corresponding ROM will store the coordinates of the individual vials.

In summary, this invention frees the user from the trouble of inputting control data whenever a new automatic sample changer is installed and hence measurements can be carried out more speedily and effortlessly. The invention is also adapted to prevent wasteful measurements caused by input errors.

What is claimed is:

1. A measuring device comprising:

an automatic sample changer for carrying a plurality of samples thereon, said automatic sample changer including motor means for changing positions of said samples, a memory device in which control data for each of different kinds of automatic sample changers are preliminarily stored, and a first connector through which said automatic sample changer receives control signals for controlling motions of said motor means and transmits data stored in said memory device; and a main body containing a second connector which is connectable with said first connector, a readout means for reading out said control data from said memory device, a drive control means for using the control data received by said readout means to generate said control signal and to transmit the generated control signal through said second connector.

2. The measuring device of claim 1 wherein said automatic sample changer includes a circular disk which is rotatable around a central shaft thereof connected to said motor means, said plurality of samples being placed in a circle around said central shaft.

3. The measuring device of claim 1 which is a spectrometer, having a light source for emitting light, an optical means for directing said light to a light incident position on said automatic sample changer, and means for detecting and analyzing light which has passed through said automatic sample changer.

4. The measuring device of claim 2 which is a spectrometer, having a light source for emitting light, an optical means for directing said light to a light incident position on said automatic sample changer, and means for detecting and analyzing light which has passed through said automatic sample changer.

5. The measuring device of claim 4 wherein said control data for each of different kinds of automatic sample changers include angles of rotation by said motor means by which said samples on said automatic sample changer can be brought to said light incident position.

6. The measuring device of claim 1 further comprising an input device through which data on the samples on said automatic sample changer are inputted to said memory device.

7. The measuring device of claim 6 further comprising a display device for displaying thereon selected data stored in said memory device.

8. The measuring device of claim 2 wherein said motor means includes a stepping motor adapted to rotate by a specified angle for each pulse signal received.

9. The measuring device of claim 4 wherein said motor means includes a stepping motor adapted to rotate by a specified angle for each pulse signal received.

10. The measuring device of claim 5 wherein said motor means includes a stepping motor adapted to rotate by a specified angle for each pulse signal received.

* * * * *